United States Patent [19]

Kawahara

[11] Patent Number: 4,882,575
[45] Date of Patent: Nov. 21, 1989

[54] MONITOR FOR BLOCKED CONDITION IN TUBE FOR FLUID INFUSION PUMP

[75] Inventor: Masafumi Kawahara, Nara, Japan

[73] Assignee: Sharp Kabushiki Kaisha, Osaka, Japan

[21] Appl. No.: 145,141

[22] Filed: Jan. 19, 1988

[30] Foreign Application Priority Data

| Jan. 28, 1987 | [JP] | Japan | 62-19054 |
| Jan. 30, 1987 | [JP] | Japan | 62-20887 |
| Feb. 4, 1987 | [JP] | Japan | 62-23969 |

[51] Int. Cl.$^4$ ............................................. G08B 21/00
[52] U.S. Cl. .............................. 340/608; 128/DIG. 13
[58] Field of Search ............... 340/603, 606, 608, 611; 128/DIG. 12, DIG. 13; 417/18

[56] References Cited

U.S. PATENT DOCUMENTS

| 3,799,702 | 3/1974 | Weishaar | 128/DIG. 12 X |
| 4,394,862 | 7/1983 | Shim | 128/DIG. 13 X |
| 4,526,574 | 6/1985 | Pekkarinen | 128/DIG. 13 X |
| 4,563,179 | 1/1986 | Sakai | 128/DIG. 13 X |
| 4,648,869 | 3/1987 | Bobo, Jr. | 604/118 X |

Primary Examiner—Joseph A. Orsino
Assistant Examiner—Jeffery A. Hofsass
Attorney, Agent, or Firm—Flehr, Hohbach, Test, Albritton & Herbert

[57] ABSTRACT

A monitor monitors for a blocked condition in a tube for a fluid infusion pump by detecting a condition of the tube by a sensor at predetermined time intervals and identifying a blocked condition in this tube by analyzing the detected values according to a specified criterion.

17 Claims, 8 Drawing Sheets

MONITOR FOR BLOCKED CONDITION IN TUBE FOR FLUID INFUSION PUMP

BACKGROUND OF THE INVENTION

This invention relates to a monitor for a blocked condition in a tube for a fluid infusion pump and more particularly to such a device for monitoring an upstream blockage, or a blocked condition in a tube between a bag containing a medical solution and a pump head.

A high degree of reliability is required of the operation of a fluid infusion pump for a medical use. For this reason, such a pump is required to be provided with many kinds of self-monitoring functions. One of such required functions relates to the detection of a blocked condition in a tube used for fluid infusion. A blocked condition in a tube between the pump and the bag containing a medical solution and the like is referred to as an upstream blockage. Two of the common causes of the upstream blockage are an upstream clamp which is inadvertently left closed and a clogged upstream filter. Even if the pump is operated continuously the fluid fails to be transported to the patient unless the blocked condition in the tube is detected and removed.

SUMMARY OF THE INVENTION

It is therefore an object of the present invention to provide a device for constantly monitoring for a blocked condition in a tube such that an upstream blockage can be dependably detected and the reliability of a fluid pump can be improved.

The above and other objects of the present invention are achieved by providing a monitor for a blocked condition in a tube for a fluid infusion pump which uses a sensor to detect the expansion or the internal pressure of the tube. The values of pressure detected by the sensor at certain time intervals are analyzed and an abnormal condition in the tube is identified by analyzing the magnitudes of these measured values according to a selected criterion.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION OF THE INVENTION

Figure 1:
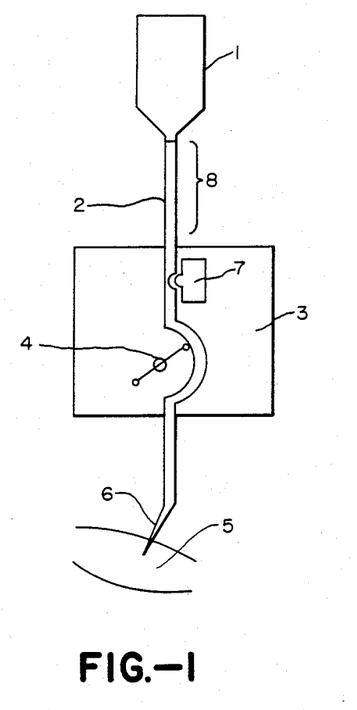
FIG. 1 is a schematic drawing of a monitor embodying the present invention

The structure of a monitor embodying the present invention for a blocked condition in a tube for a fluid infusion pump is described first by way of FIG. 1 wherein numeral 1 indicates a bag containing a fluid solution. The solution contained in the bag 1 is adapted to be transported through a tube 2 connected to this bag 1 to a pump system 3. The pump system 3 includes within itself a pump head 4 of a rotary structure which is adapted to squeeze the tube 2 peristaltically with its end part such that a predetermined quantity of the solution is infused into a patient 5 through a needle 6 attached to an end section of the tube 2. The pump system 3 further includes a sensor 7 adapted to detect the degree of expansion of the tube 2 between the bag 1 and the pump head 4 either by an active or passive method. Different types of sensors may be used for this purpose. It may be a pressure sensor, a strain gauge, an ultrasonic wave sensor or an optical sensor. With the sensor 7 constantly monitoring the expansion of the tube 2 by a specified method, a blocked condition in the upstream section of the tube 2 (indicated by numeral 8 in FIG. 1) can be detected. Next, the monitoring method by the sensor 7 is explained for a situation in which the sensor 7 is a pressure sensor.

Figure 2A:
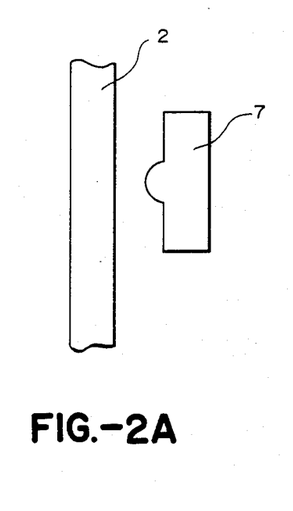
FIGS. 2A, 2B and 2C are schematic drawings for explaining the creeping phenomenon.
Figure 2B:
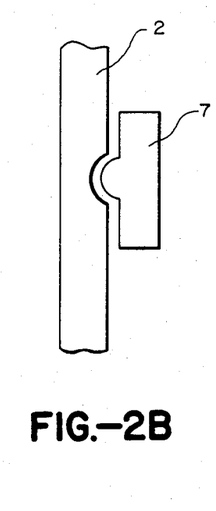
Figure 2C:
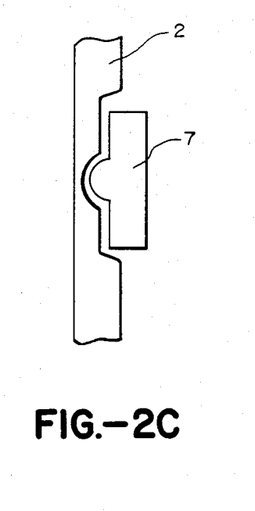
Figure 3:
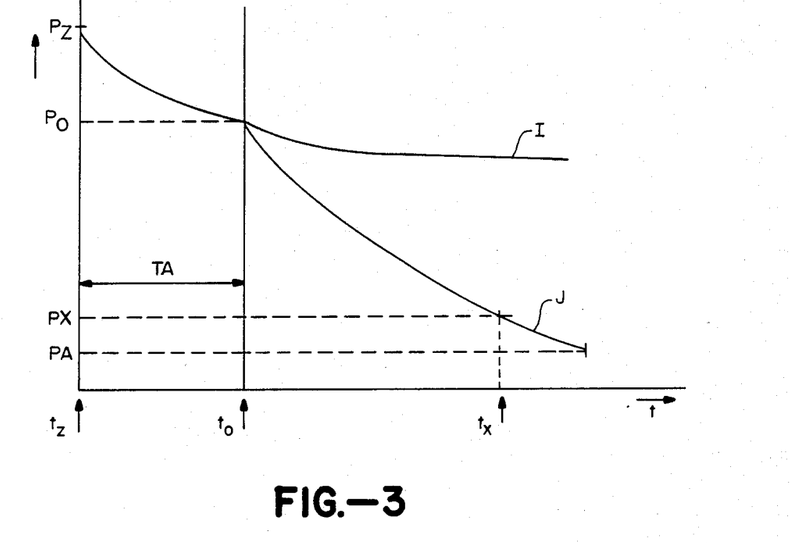
FIG. 3 is a schematic graph showing the time rate of change in the pressure measured by the sensor of FIG. 1.

When the pressure sensor 7 comes to touch the tube 2, the tube 2 tends to stay in contact with the sensor 7 because of its material and other characteristics. In other words, as long as a pressure is being applied, the tube 2 moves in the direction of reducing its expansion with time even if there is no upstream blockage. This phenomenon is called a creeping phenomenon and is illustrated in FIGS. 2A, 2B and 2C. The sensor 7 is connected to a door (not shown) for the pump head 4 and FIG. 2A shows the situation where this door for the pump head 4 is not open yet and the tube 2 is not in contact with the sensor 7. When the door for the pump head 4 is closed, however, the sensor 7 is moved correspondingly and presses the tube 2 as shown in FIG. 2B. As time passes thereafter, the tube 2 shrinks gradually as shown in FIG. 2C, being pressed by the sensor 7. The rate at which the tube 2 shrinks by this creeping phenomenon is nearly logarithmic. FIG. 3 shows the manner in which the detected value of pressure by the sensor 7 changes with time. In the graph of FIG. 3, the vertical axis represents the pressure P inside the tube 2 as measured by the sensor 7. It is to be understood that the smaller the value of P, the more the tube 2 shrinks. The horizontal axis represents the time t.

With reference to FIG. 3, $t_z$ represents the time at which the door for the pump head 4 is closed, $P_z$ representing the value of the pressure P at this time, or the initial pressure, and $t_0$ represents the time at which the operation of the pump system 3 is started. Thus, the time interval between $t_z$ and $t_0$ represents the period during which the tube 2 is set to the pump head 4, the door for the pump head 4 is closed and the pump system 3 begins to operate (for example, by starting a motor for this pump system 3). Since no infusion takes place during this time interval from $t_z$ to $t_0$ independently of the presence or absence of an upstream blockage, there is no significant change in the expansion of the tube 2 and the change in pressure P is accordingly small in this time interval.

After the operation of the pump system 3 is started (that is, after $t_0$), however, the pressure P drops inside the tube 2. If there is no upstream blockage, the pressure P drops as shown by Curve I in FIG. 3. Infusion of the solution is effected by the rotation of a motor (not shown in FIG. 1 but shown at 13 in FIG. 4) attached to the pump head 4 such that a predefined quantity of the solution is infused per unit rotation of this motor. After the motor has rotated a specified number of times (such as one revolution), the solution originally inside the tube 2 is removed therefrom but since a new supply of the solution is received from the bag 1, the value of pressure detected by the sensor 7 in contact with this tube 2 does not change over what corresponds to the aforementioned creeping phenomenon.

If there is an upstream blockage, however, the pressure P drops faster as shown by Curve J because there is no supply of solution from the bag 1 and the quantity of the solution inside the tube 2 decreases more rapidly. Thus, the shrinking of the tube 2 and the rotation of the motor are intimately related. According to one embodiment of the present invention, the upstream blockage, or an abnormal condition caused thereby, is detected by comparing the measured value of the pressure P with a predefined reference value $P_x$ before a situation arises wherein no solution is infused at all although the pump system 3 is operating. Once such an abnormal situation is detected, a warning signal is outputted either as a visual display or by a sound as will be explained below and the pump operation is stopped so as to prevent the abnormal condition from continuing to exist. The aforementioned reference value $P_x$ is set larger than the value $P_a$ of pressure when the tube 2 is completely blocked such that a warning signal indicating the abnormal condition can be outputted before the internal pressure of the tube 2 reaches such a value, that is, while the infusion is still continuing.

With reference to FIG. 3, therefore, it is at time $t_x$ when the abnormal condition is detected and a warning is issued such that a doctor or a nurse can take an appropriate step. The reference value $P_x$ may be either a fixed value or determined as a specified fraction of $P_Z$ or $P_0$.

Figure 4:
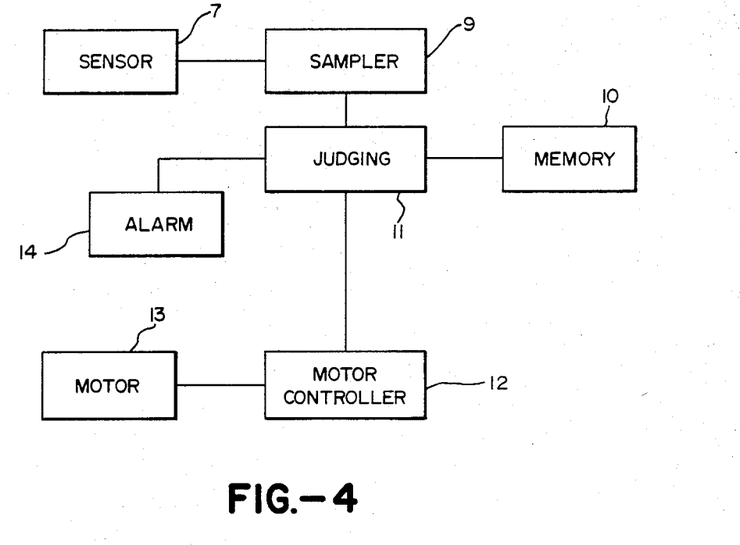
FIG. 4 is a block diagram of a monitor embodying the present invention.

With reference next to FIG. 4 which is a block diagram of the monitor of which the operation was briefly described above, the pressure P detected by the sensor 7 is sampled by a sampler 9, or a device having a sampling capability. The aforementioned reference value $P_X$ is stored in a memory device 10 and a judging circuit 11 serves to compare the values of the pressure P sampled by the sampler 9 with the reference value $P_X$ stored in this memory device 10. If it is determined by the judging circuit 11 that the pressure inside the tube 2 is greater than this reference value $P_X$, no abnormality signal is transmitted from the judging circuit 11 to a motor controller 12 which is for controlling the motion of the motor 13 for rotating the pump head 4. Accordingly, the motor 13 is operated and the pump head 4 is rotated such that the infusion operation is resumed. If the judging circuit 11 determines that the pressure value detected by the sensor 7 is less than the reference value $P_X$, however, an abnormality signal indicative of the occurrence of an abnormal condition is transmitted from the judging circuit 11 to the motor controller 12, causing the motion of the motor 13, and hence the operation of the pump head 4 to be stopped. At the same time, the judging circuit 11 activates an alarm 14, which may be a buzzer, a vocal output device or the like or a visual device such as a liquid crystal display device or a light-emitting diode. A microcomputer may comprise the sampler 9, the memory device 10 and the judging circuit 11.

Figure 5:
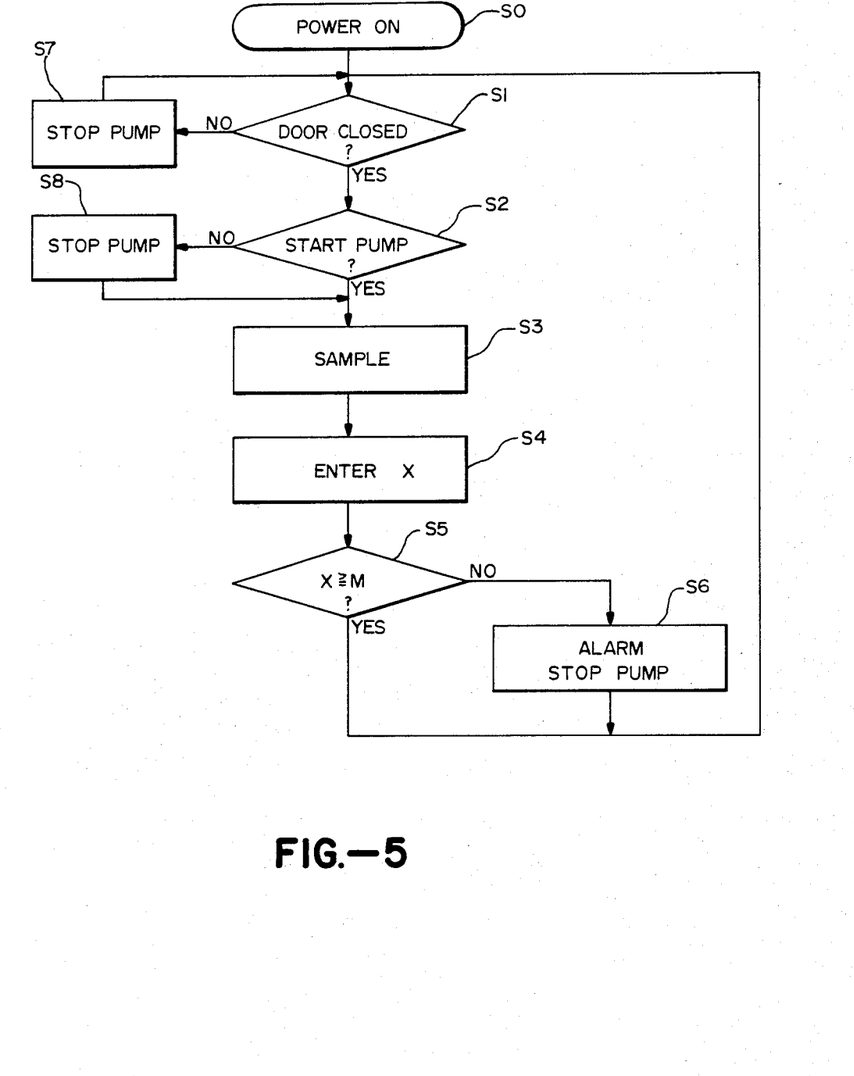
FIG. 5 is a flowchart for the operation of the monitor of FIG. 4.

The operation of the monitor described above is explained next by way of the flowchart of FIG. 5. After power is switched on (S0), it is determined whether the door for the pump head 4 is opened or not (S1) and whether the intended time to start the motor 13 has been reached or not (S2). Unless the answers in Steps S1 and S2 are both YES, the pump head 4 remains stopped (S7 and S8). If they are both YES, a pressure value P detected by the sensor 7 is sampled by the sampler 9 (S3) and the sampled value P is inputted into a register X in the judging circuit 11 (S4) to have it compared with the reference value $P_X$ which is preliminarily stored in the memory device 10 (S5). If the sampled pressure value P now stored in the register X is less than the reference value $P_X$, the alarm 14 is activated and the operation of the pump is stopped (S6).

If the reference value $P_X$ is not a predefined constant but a certain fraction of $P_Z$ or $P_0$ as explained above in connection with FIG. 3, an additional memory device is provided for storing such pressure value and a circuit for calculating the fraction thereof with which the sampled pressure value P is compared. Such a fraction, furthermore, may be either a preliminarily stored constant value or inputted through an input device such as a keyboard (not shown).

Figure 6:
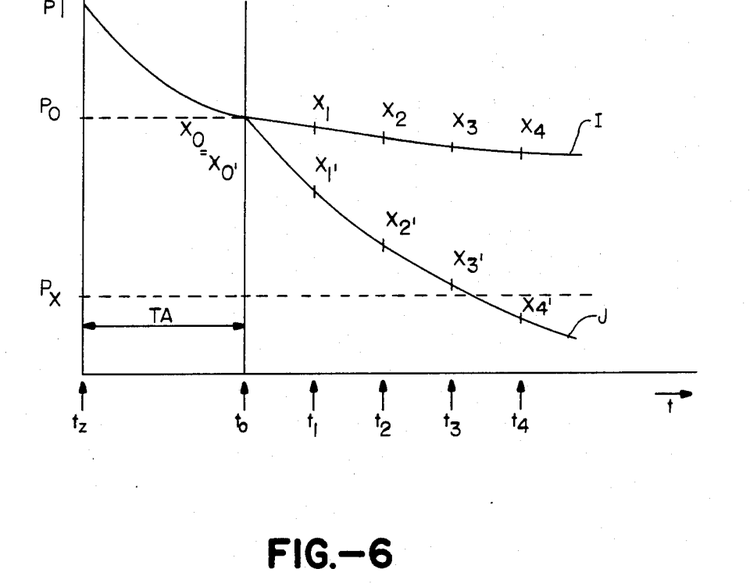
FIG. 6 is another schematic graph showing the time rate of change in the pressure measured by the sensor of FIG. 1 according to another sampling schedule.

Another monitor embodying the present invention operating on a different principle is described next by way of the graph of FIG. 6 showing curves which are similar to those described above in FIG. 3 and hence indicated by I and J again. With this monitor, the pressure value P detected by the sensor 7 is sampled after time $t_0$ once for every complete revolution of the motor for the pump 4. The time points at which a pressure value P is sampled are indicated in FIG. 6 by $t_1$, $t_2$, etc. and the corresponding sampled values are indicated by $x_1$, $x_2$, etc. if there is no abnormality and pressure changes as shown by Curve I and by $x_1'$, $x_2'$, etc. if there is an upstream blockage and pressure changes as shown by Curve J.

As explained generally above, Curve I shows only the effect of the creeping phenomenon and hence the differences $D_n$ defined by $x_{n-1} - x_n$ (where $n = 1, 2, 3 \ldots$) are relatively small. In the case of an upstream blockage, by contrast, the differences $D_n'$ defined by $x_{n-1}' - x_n'$ (where $n = 1, 2, 3 \ldots$) are relatively large. If the blockage is very serious, the initial value $x_1'$ may be already comparable to $P_X$ defined above in connection with FIG. 3.

Any of many criteria may be used to identify an abnormal condition such as the difference $D_n'$ being greater than a certain constant, $x_n'$ being smaller than a certain fraction of $P_0$ and $x_n$ becoming smaller than $P_X$.

Figure 7:
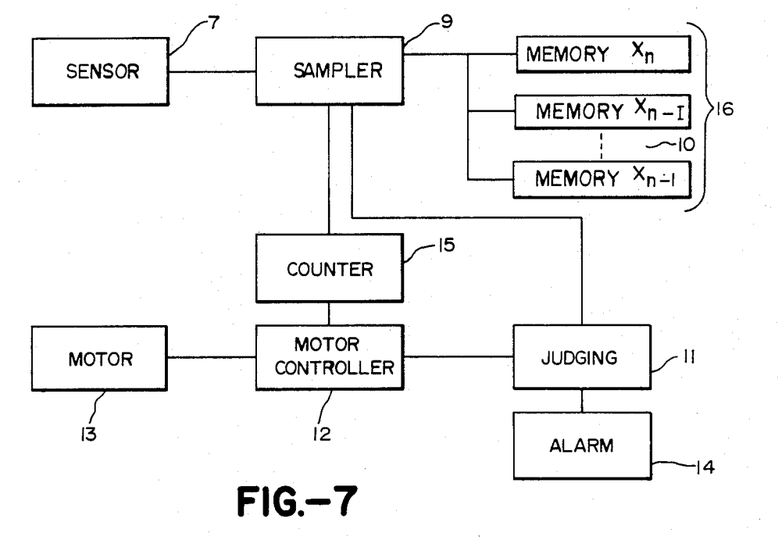
FIG. 7 is a block diagram of another monitor embodying the present invention.

FIG. 7 is a block diagram of a monitor operable on the principle described above in connection with FIG. 6. In FIG. 7, components which are substantially identical or at least comparable to those already described by way of FIG. 4 are indicated by the same numerals. A monitor represented by this block diagram is characterized as having a rotation counter 15 and memory devices 16 (or $M_1$, $M_2$, ...). The rotation counter 15 is connected to the motor controller 12 and counts the number of revolutions of the motor 13, outputting a signal to the sampler 9 whenever the motor 13 makes a complete revolution. Whenever this outputted signal is received by the sampler 9, a new pressure value is sampled and the pressure values thus sampled are sequentially stored in these memory devices 16. With reference to FIG. 7, the memory device $M_1$ stores the most recently sampled pressure value. When a newly sampled pressure value is stored in this memory device $M_1$, the values which have been stored in the memory devices $M_1$, $M_2$, ... up to this moment are shifted into the memory devices $M_2$, $M_3$, ..., respectively. The values stored in these memory devices 16 are used by the judging circuit 11 to determine whether a preselected criterion for identifying an abnormal condition has been satisfied.

Figure 8:
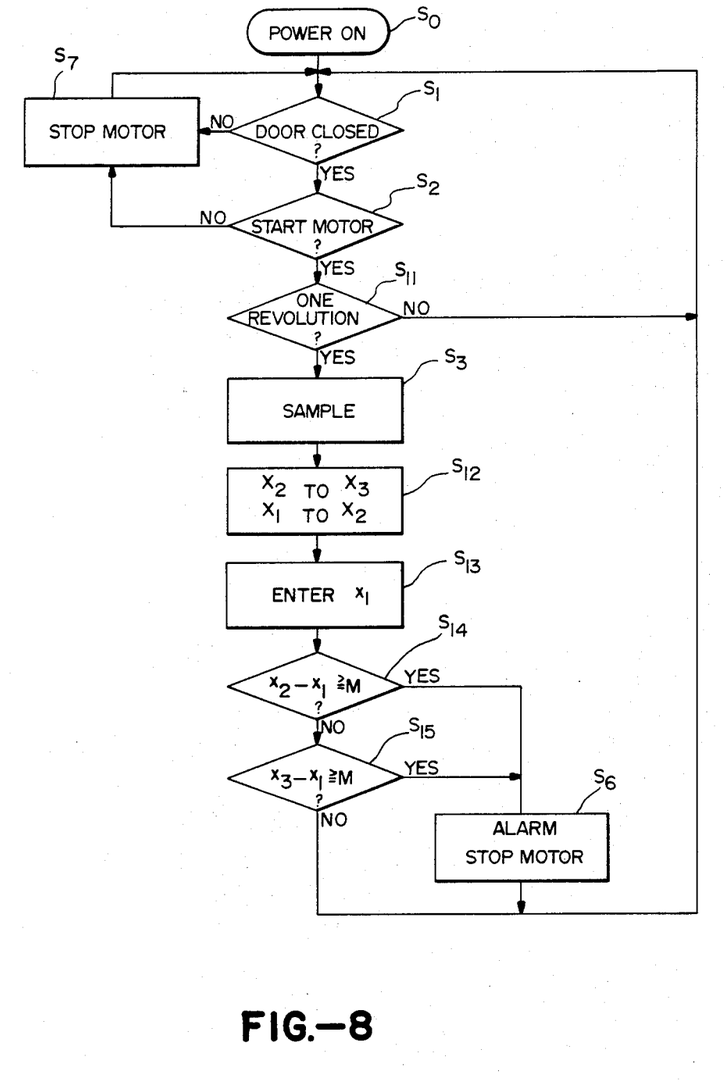
FIG. 8 is a flowchart of the operation of the monitor of FIG. 7.

FIG. 8 is a flowchart for explaining the operation of a monitor described above in connection with the block diagram in FIG. 7 and programmed to identify an abnormal condition when the difference $D_n'$ is greater than a preselected reference value Y. For this flowchart, only three memory devices $M_1$, $M_2$ and $M_3$ are used and the steps which are substantially identical to those in the flowchart of FIG. 5 are indicated by the same step numbers and will not be explained again. After the time to start the motor 13 is reached (YES in S2), the monitor waits until the rotation counter 15 determines that the motor 13 has made one complete revolution (S11) and, when it is so determined, the sampler 9 samples the newest pressure value determined by the sensor 7 (S3) but before this new pressure value is stored in the first memory device $M_1$ (S13), the content of the second memory device $M_2$ is shifted to the third memory device $M_3$ and that of the first memory device $M_1$ is shifted to the second memory device $M_2$ (S12). In other words, the contents of the memory devices 16 are updated in Steps S12 and S13. If the pressure values stored in the memory devices $M_1$, $M_2$ and $M_3$ are indicated also by $M_1$, $M_2$ and $M_3$, respectively, the difference values $M_2-M_1$ and $M_3-M_1$ are compared with the aforementioned selected reference value Y (S14 and S15) and unless these difference values are found to be less than this reference value Y, the monitor determines that an abnormal condition has occurred and outputs an alarm, stopping the operation of the motor 13 (S6).

Figure 9:
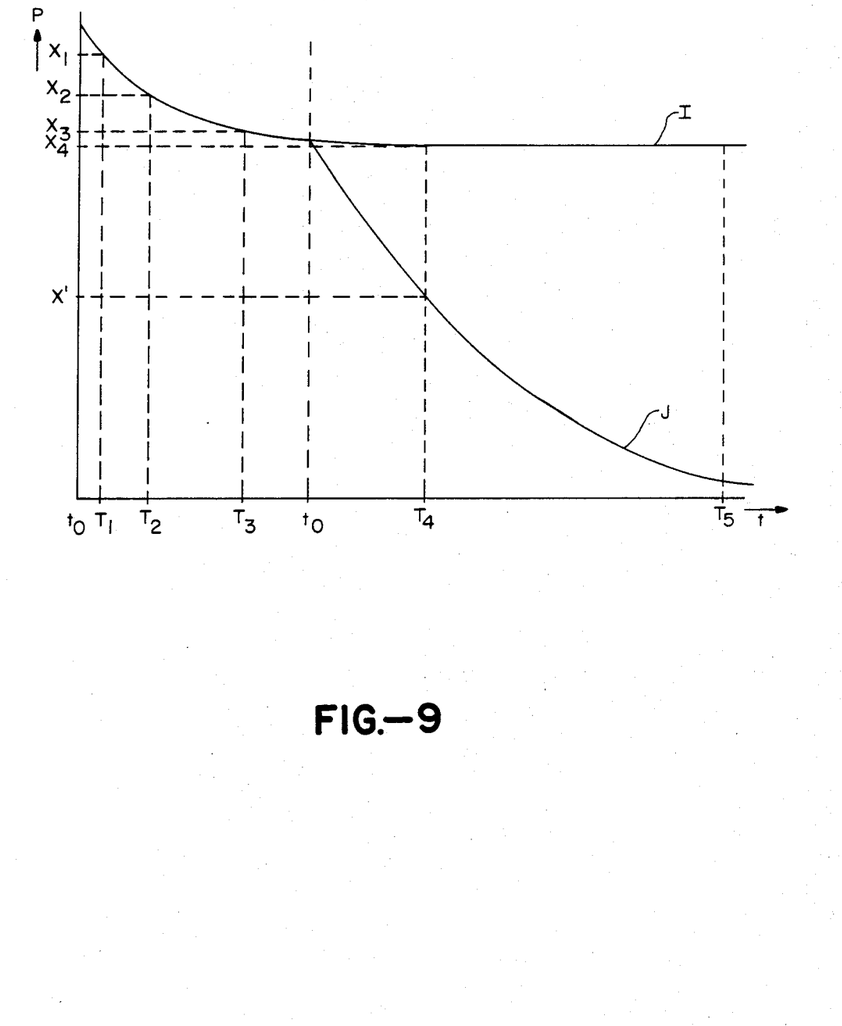
FIG. 9 is still another schematic graph showing the time rate of change in the pressure measured by the sensor of FIG. 1 according to still another sampling schedule.

FIG. 9 is another graph showing the time rate of change of pressure measured by the sensor 7 of FIG. 1 for explaining the structure and operation of still another monitor embodying the present invention. The monitor according to this embodiment is characterized as sampling pressure values at unequal time intervals. Since Curves I and J of FIGS. 3 and 6 and drawn again in FIG. 9 are nearly logarithmic in shape, it is more advantageous to gradually keep increasing the intervals between successive sampling operations. This is because the tube 2 shrinks substantially if the time interval between $t_z$ and $t_0$ is sufficiently long and the change in the expansion of the tube 2 becomes very slow after $t_0$ such that an abnormal condition cannot be identified unless observation is taken over a long period of time. The monitor according to this embodiment, therefore, is characterized as sampling pressure values at times $T_1$, $T_2$, $T_3$, $T_4$, at gradually increasing intervals after the initial time $t_z$. The sampled pressure values taken at $T_1$, $T_2$ and $T_3$ are indicated by $X_1$, $X_2$ and $X_3$, those at $T_4$, $T_5$, ... are indicated by $X_4$, $X_5$, ... along Curve I and by $X_4'$, $X_5'$, ... along Curve J.

As explained above with reference to FIG. 6, several criteria may be considered by which the monitor can identify an abnormal condition from the measured pressure value $X_4$ or $X_4'$ at $T_4$ with reference to FIG. 9. Firstly, the monitor may be programmed to identify an abnormal condition by detecting that $X_4'$ is smaller than an earlier sampled value by more than a predetermined magnitude. Secondly, such identification may be made when $X_4'$ is smaller than a predetermined fraction of an earlier sampled value. Thirdly, the criterion may be expressed by $D_2' \geq D_1$ where $D_1 = X_1 - X_3$ and $D_2' = X_2 - X_4'$. If an abnormal condition by any such criterion, the monitor outputs a warning as explained above.

Figure 10:
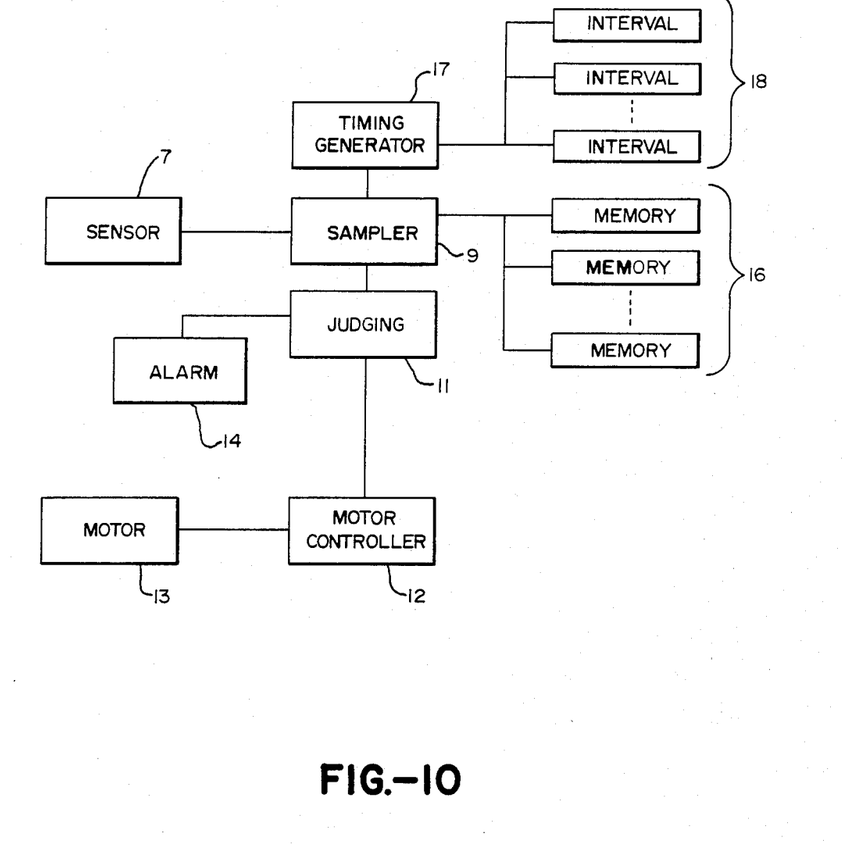
FIG. 10 is a block diagram of still another monitor embodying the present invention.

FIG. 10 is a block diagram of a monitor which may sample pressure values and identify an abnormal condition by any of such criteria described above. Components which are substantially identical or at least comparable to those already described in connection with FIGS. 4 and 7 are indicated by the same numerals and are not explained again. The block diagram of FIG. 10, and hence a monitor described by such a block diagram is characterized as having a timing generator 17 for operating the sampler 9 at a predetermined timing sequence and memory devices 18 for storing a predetermined set of time interval data ($T_2-T_1$, $T_3-T_2$, etc.). The timing generator 17 is adapted to output pulse signals sequentially to the sampler 9 according to the time interval data stored in these memory devices 17.

Figure 11:
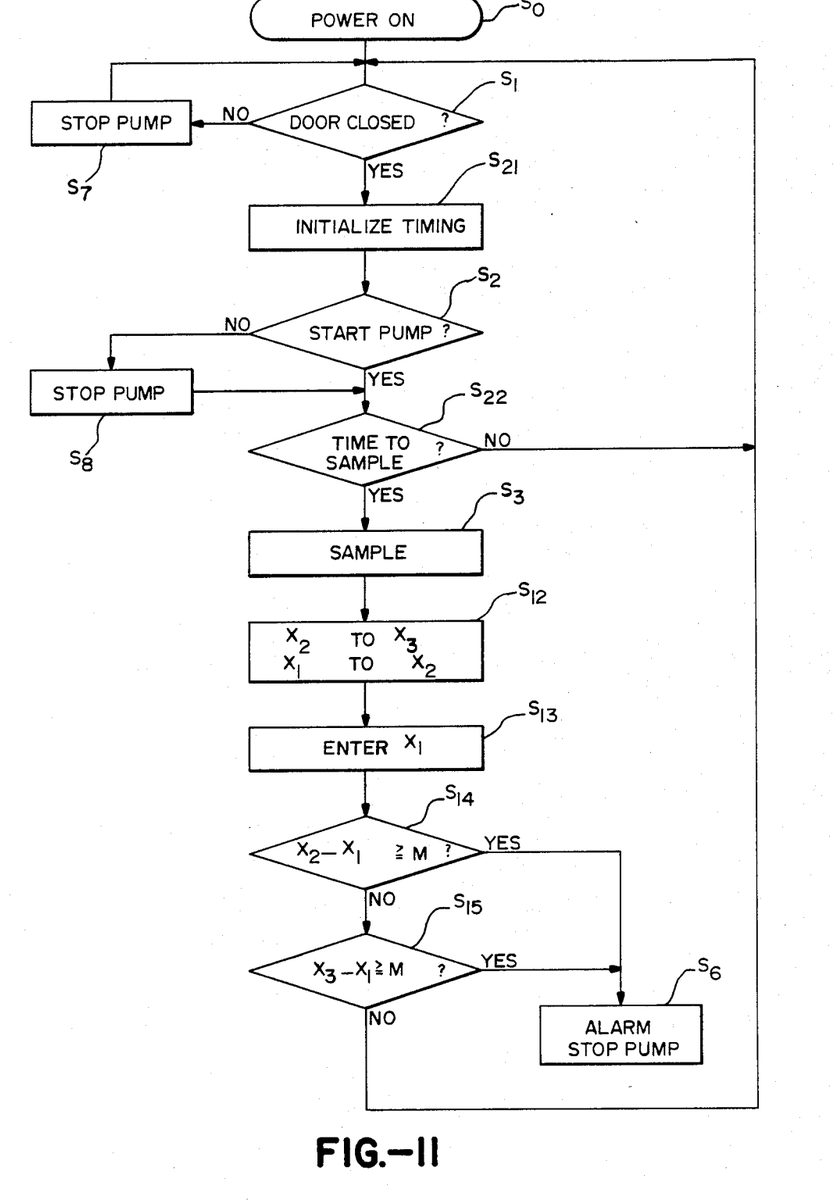
FIG. 11 is a flowchart of the operation of the monitor of FIG. 10.

FIG. 11 is a flowchart for showing the operation of a monitor described above in connection with the block diagram of FIG. 10 using only three memory devices $M_1$, $M_2$ and $M_3$ as in the case of FIG. 8 and the first of the three exemplary criteria for identifying an abnormal condition. In FIG. 11, the steps which are substantially identical to those in the flowchart of FIGS. 5 and/or 8 are similarly indicated by the same step numbers. Thus, the flowchart of FIG. 11 is characterized by the step of initializing the timing generator 17 (S21) after each sampling operation and the step of determining whether the next sampling time has arrived (S22).

The foregoing description of preferred embodiments of the present invention has been presented for purposes of illustration and description. It is not intended to be exhaustive or to limit the invention to the precise form disclosed. Many modifications and variations are possible in light of the above teaching. For example, the sampling frequency of a monitor explained by way of FIGS. 6-8 above need not correspond to one revolution of the motor, that is, the sampling frequency may correspond to one-half revolution or an integral number of revolutions greater than one. Since both the block diagram of FIG. 10 and the flowchart of FIG. 11 apply to a particular criterion by which the presence of an abnormal condition is identified, the block diagram and the flowchart must be appropriately modified if a different criterion is used as explained above in connection with FIGS. 7 and 8. The criterion may be a comparison between two difference values $D_n$ and $D_{n+1}$ respectively defined by $X_n - X_{n-3}$ and $X_{n+1} - X_{n-2}$ where $X_{n+1}$ represents the most recently sampled value, $X_n$ represents the second most recently sampled value, etc. and it is concluded that an abnormal condition has occurred if $D_{n+1}$ is greater than or equal to $D_n$. In this case, the monitor is also provided with subtractor circuits for outputting the aforementioned difference values and a comparator circuit for comparing $D_n$ and $D_{n+1}$. Other similar criteria may be used by considering relative magnitudes of sampled pressure values to identify an abnormal condition. Monitors of the type explained by FIGS. 9-11 may be summarized generally as sampling pressure values detected by the sensor 7 at times separated by a given series of intervals, storing the most recently obtained sample value $X_n$ and the previously obtained values $X_{n-1}, X_{n-2}, \ldots$ and considering the differences between $X_n$ and $X_{n-m}$ ($m=1,2,\ldots$) to determine, for example, whether the expansion of the tube 2 is becoming zero between $X_n$ and $X_{n-m}$. The types of acceptable criteria generally include comparison between $X_n$ and $X_{n-m}$ ($m=1,2,3,\ldots$), magnitude of the quotient $X_n/X_{n-m}$ ($m=1,2,3,\ldots$) and comparison between $D_{n+1}$ and $D_n$ defined above.

In summary, any modifications and variations that may be apparent to a person skilled in the art are intended to be included within the scope of this invention.

What is claimed is:

1. A monitor for a blocked condition in a tube for a fluid infusion pump having a fluid container connected to said tube and head means for operating on said tube to cause a fluid transportation through said tube, said monitor comprising detector means for detecting selectively at times separated by a constant interval or at times separated by uniformly increasing intervals a condition of said tube between said fluid container and said head means, and control means for monitoring for a blocked condition in said tube by comparing a most recently outputted value from said detector means selectively with a predetermined constant value or an earlier outputted value from said detector means.

2. The monitor of claim 1 wherein said control means include judging means for comparing said values detected by said detector means with a reference value and identify a blocked condition in said tube on the basis of judgment by said judging means.

3. The monitor of claim 2 further comprising warning means for outputting an alarm signal in response to said judgment by said judging means.

4. The monitor of claim 3 wherein said alarm signal is a sound signal.

5. The monitor of claim 3 wherein said alarm signal is a visual signal.

6. The monitor of claim 2 wherein said detector means include a sensor adapted to come in contact with said tube in coordination with a closing motion of a door.

7. The monitor of claim 6 wherein said reference value is determined from the value of internal pressure of said tube when said sensor comes in contact with said tube.

8. The monitor of claim 2 wherein said reference value is determined from the value of internal pressure of said tube when said pump begins to operate.

9. The monitor of claim 2 further comprising stopping means for stopping the operation of said pump in response to said judgment by said judging means.

10. A monitor for a blocked condition in a tube for a fluid infusion pump having a fluid container connected to said tube and head means for operating on said tube to cause a fluid transportation through said tube, said monitor comprising detector means for detecting a condition of said tube between said fluid container and said head means, sampling means for sampling values detected by said detector means at times with increasing intervals therebetween, memory means for storing values sampled by said sampling means, and judging means for comparing said sampled values and identifying as blocked condition in said tube according to a specified criterion, whereby said monitor monitors for a blocked condition in said tube.

11. The monitor of claim 10 wherein said judging means compare according to said specified condition the most recently sampled one of said values with a specified reference value.

12. The monitor of claim 10 wherein said judging means compare according to said specified criterion the most recently sampled one of said values with a specified fraction of one of previously obtained ones of said values.

13. The monitor of claim 10 wherein said judging means compare a first difference between the most recently sampled one and the fourth most recently sampled one of said values and a second difference between the second most recently sampled one and the fifth most recently sampled one of said values and identifies a blocked condition in said tube unless said first difference is smaller than said second difference.

14. The monitor of claim 10 further comprising warning means for outputting an alarm signal indicative of an occurrence of a blocked condition in said tube when said judging means identifies said blocked condition.

15. The monitor of claim 14 wherein said alarm signal is a sound signal.

16. The monitor of claim 14 wherein said alarm signal is a visual signal.

17. The monitor of claim 10 further comprising stopping means for stopping the operation of said head means when said judging means identify said blocked condition.

* * * * *